United States Patent
Ding et al.

(10) Patent No.: US 12,421,236 B2
(45) Date of Patent: Sep. 23, 2025

(54) SEVEN-MEMBERED HETEROCYCLIC DERIVATIVE ACTING AS KRAS G12C MUTANT PROTEIN INHIBITOR

(71) Applicants: Chia Tai Tianqing Pharmaceutical Group Co., Ltd., Lianyungang (CN); Medshine Discovery Inc., Nanjing (CN)

(72) Inventors: Charles Z. Ding, Shanghai (CN); Shuhui Chen, Shanghai (CN)

(73) Assignees: Chia Tai Tianqing Pharmaceutical Group Co., Ltd., Lianyungang (CN); Medshine Discovery Inc., Nanjing (CN)

( * ) Notice: Subject to any disclaimer, the term of this patent is extended or adjusted under 35 U.S.C. 154(b) by 889 days.

(21) Appl. No.: 17/621,621

(22) PCT Filed: Jun. 24, 2020

(86) PCT No.: PCT/CN2020/098070
§ 371 (c)(1),
(2) Date: Dec. 21, 2021

(87) PCT Pub. No.: WO2020/259573
PCT Pub. Date: Dec. 30, 2020

(65) Prior Publication Data
US 2022/0372036 A1  Nov. 24, 2022

(30) Foreign Application Priority Data

Jun. 25, 2019 (CN) .......................... 201910556652.6
Oct. 17, 2019 (CN) .......................... 201910990276.1
Dec. 31, 2019 (CN) .......................... 201911410783.X

(51) Int. Cl.
*C07D 471/22* (2006.01)
*C07D 498/22* (2006.01)

(52) U.S. Cl.
CPC ......... *C07D 471/22* (2013.01); *C07D 498/22* (2013.01)

(58) Field of Classification Search
CPC .................................................. C07D 471/22
See application file for complete search history.

(56) References Cited

U.S. PATENT DOCUMENTS

2019/0177338 A1    6/2019  Kettle et al.
2023/0357272 A1*  11/2023  Chen ...................... A61P 35/00

FOREIGN PATENT DOCUMENTS

| CN | 105189456 A | 12/2015 |
| CN | 106488910 A | 3/2017 |
| WO | WO 2014/152588 A1 | 9/2014 |
| WO | WO 2018/064510 A1 | 4/2018 |
| WO | WO 2018/143315 A1 | 8/2018 |
| WO | WO 2018/206539 A1 | 11/2018 |
| WO | WO 2018/217651 A1 | 11/2018 |
| WO | WO 2018/218070 A2 | 11/2018 |
| WO | WO 2018/218071 A1 | 11/2018 |
| WO | WO 2018/237084 A1 | 12/2018 |
| WO | WO 2019/051291 A1 | 3/2019 |

OTHER PUBLICATIONS

International Search Report for PCT/CN2020/098070 dated Sep. 29, 2020.

* cited by examiner

*Primary Examiner* — Andrew D Kosar
*Assistant Examiner* — Connor K English
(74) *Attorney, Agent, or Firm* — Knobbe, Martens, Olson & Bear, LLP

(57) ABSTRACT

A class of KRAS G12C mutant protein inhibitors, specifically disclosing the compound shown in formula (I), and an isomer and a pharmaceutically acceptable salt thereof.

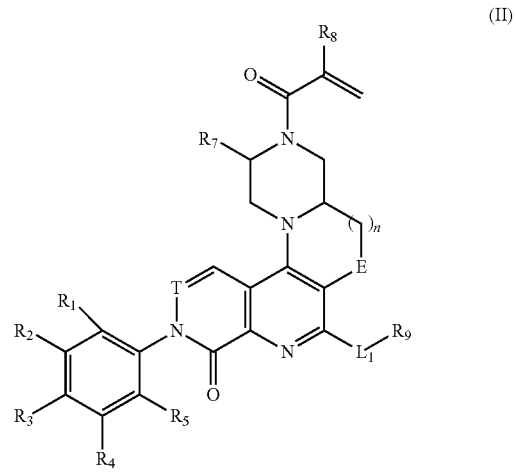

19 Claims, No Drawings

SEVEN-MEMBERED HETEROCYCLIC DERIVATIVE ACTING AS KRAS G12C MUTANT PROTEIN INHIBITOR

CROSS REFERENCE TO RELATED APPLICATION

This application is a U.S. National Phase Application of PCT International Application Number PCT/CN2020/098070, filed on Jun. 24, 2020, designating the United States of America and published in the Chinese language, which is an International Application of and claims the benefit of priority to Chinese Patent Application No. 201910556652.6, filed on Jun. 25, 2019, Chinese Patent Application No. 201910990276.1, filed on Oct. 17, 2019, and Chinese Patent Application No. 201911410783.X, filed on Dec. 31, 2019. The disclosures of the above-referenced applications are hereby expressly incorporated by reference in their entireties.

TECHNICAL FIELD

The present invention relates to a new type of KRAS G12C mutant protein inhibitor, in particular to a compound of formula (I), and an isomer and a pharmaceutically acceptable salt thereof.

BACKGROUND

The first RAS oncogene was found in rat sarcoma, hence the name. RAS protein is a product expressed by RAS gene, and refers to a class of closely related monomer globulins consisting of 189 amino acids with a molecular weight of 21 KDa. It can bind to guanosine triphosphate (GTP) or guanosine diphosphate (GDP). The active state of the RAS protein has an influence on the growth, differentiation and skeleton of cells, the transportation and secretion of proteins, and the like. The activity of the RAS protein is regulated by binding to GTP or GDP. When binding to GDP, the RAS protein is in the dormant or "inactivated" state; when stimulated by specific upstream cell growth factors, the RAS protein is induced to exchange GDP and bind to GTP, which is referred to as the "activated" state. The RAS protein binding to GTP is able to activate downstream proteins for signaling. The RAS protein itself has weak hydrolysis activity for GTP, and is able to hydrolyze GTP to GDP. This allows the transition from the activated state to the inactivated state to be achieved. GAP (GTPase activating protein) is also required in this hydrolysis process. GAP can interact with the RAS protein to greatly promote its ability to hydrolyze GTP to GDP. Mutations in the RAS protein affect its interaction with GAP and thus its ability to hydrolyze GTP to GDP, keeping it in the activated state. The activated RAS protein continuously sends growth signal to downstream protein, which leads to the incessant growth and differentiation of cells, and ultimately to the occurrence of tumors. The RAS gene family is numerous in members, among which the subfamilies closely related to various cancers mainly include Kirsten rat sarcoma viral oncogene homolog (KRAS), Harvey rat sarcoma viral oncogene homolog (HRAS), and neuroblastoma rat sarcoma viral oncogene homolog (NRAS). It is found that approximately 30% of human tumors carry some RAS mutations, with KRAS mutations dominated, accounting for 86% of all RAS mutations. For KRAS mutations, the most common mutations occur at glycine 12 (G12), glycine 13 (G13) and glutamine 61 (Q61) residues, with the G12 mutation accounting for 83%.

The G12C mutation is a relatively common one of KRAS gene mutations, which refers to the mutation of glycine 12 to cysteine. The KRAS G12C mutation is most common in lung cancer, and occurs in about 10% of all lung cancer patients as extrapolated from data reported in the literature (Nat Rev Drug Discov 2014; 13: 828-851).

SUMMARY

The present invention provides a compound of formula (II), a pharmaceutically acceptable salt thereof or an isomer thereof,

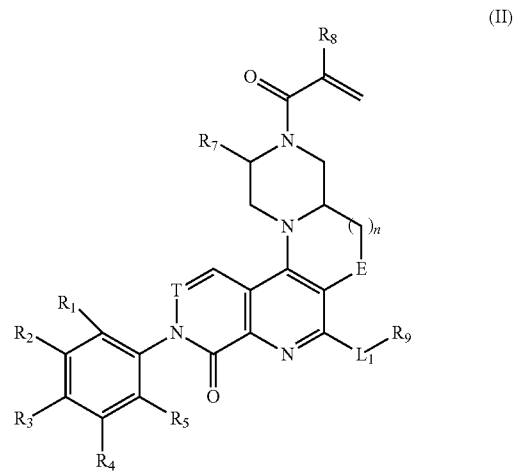

wherein,
$R_1$ is H, F, Cl, Br, I, $NH_2$ and $C_{1-3}$ alkyl, wherein the $C_{1-3}$ alkyl is optionally substituted with 1, 2 or 3 $R_a$; $R_2$, $R_3$, $R_4$ and $R_5$ are each independently selected from the group consisting of H, F, Cl, Br, I and $C_{1-3}$ alkyl, wherein the $C_{1-3}$ alkyl is optionally substituted with 1, 2 or 3 $R_b$;
T is selected from the group consisting of $C(R_6)$ and N;
$R_6$ is selected from the group consisting of H, F, Cl, Br, I and $C_{1-3}$ alkyl, wherein the $C_{1-3}$ alkyl is optionally substituted with 1, 2 or 3 $R_c$;
$R_7$ is selected from the group consisting of H and —$CH_2$—CN;
$R_8$ is selected from the group consisting of H and F;
$L_1$ is selected from the group consisting of a single bond,

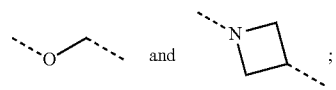

$R_9$ is selected from the group consisting of H, Cl, pyrrolidinyl and $C_{1-6}$ alkylamino, wherein the pyrrolidinyl and the $C_{1-6}$ alkylamino are optionally substituted with 1, 2 or 3 $R_d$;
E is selected from the group consisting of —O— and —N-$L_2$-$L_3$-$R_{10}$;
$L_2$ is selected from the group consisting of a single bond, —$CH_2$— and —C(=O)—;

$L_3$ is selected from the group consisting of a single bond, —$CH_2$— and

;

$R_{10}$ is selected from the group consisting of H and $C_{1-6}$ alkylamino;

$R_a$, $R_b$, $R_c$ and $R_d$ are each independently selected from the group consisting of H, F, Cl, Br, I and $CH_3$; and n is selected from 2.

In some embodiments of the present invention, provided is the compound, the pharmaceutically acceptable salt thereof or the isomer thereof, wherein $R_1$ is selected from $NH_2$, and other variables are as defined herein.

In some embodiments of the present invention, provided is the compound, the pharmaceutically acceptable salt thereof or the isomer thereof, wherein $R_2$ is selected from the group consisting of Cl and Br, and other variables are as defined herein.

In some embodiments of the present invention, provided is the compound, the pharmaceutically acceptable salt thereof or the isomer thereof, wherein $R_3$ is selected from the group consisting of H, and other variables are as defined herein.

In some embodiments of the present invention, provided is the compound, the pharmaceutically acceptable salt thereof or the isomer thereof, wherein $R_4$ is selected from the group consisting of Cl and Br, and other variables are as defined herein.

In some embodiments of the present invention, provided is the compound, the pharmaceutically acceptable salt thereof or the isomer thereof, wherein $R_5$ is selected from F, and other variables are as defined herein.

In some embodiments of the present invention, provided is the compound, the pharmaceutically acceptable salt thereof or the isomer thereof, wherein the structural unit

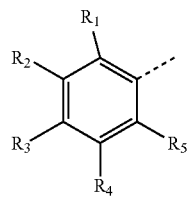

is selected from the group consisting of

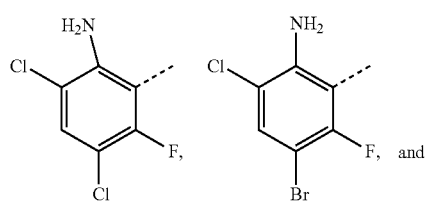

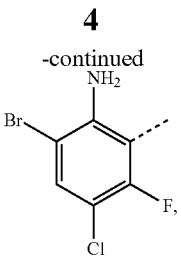

and other variables are as defined herein.

In some embodiments of the present invention, provided is the compound, the pharmaceutically acceptable salt thereof or the isomer thereof, wherein $R_6$ is selected from the group consisting of H, F, Cl, Br, I, $CH_3$, $CF_3$, $CHF_2$ and $CH_2F$, and other variables are as defined herein.

In some embodiments of the present invention, provided is the compound, the pharmaceutically acceptable salt thereof or the isomer thereof, wherein $R_6$ is selected from the group consisting of $CF_3$ and $CH_3$, and other variables are as defined herein.

In some embodiments of the present invention, provided is the compound, the pharmaceutically acceptable salt thereof or the isomer thereof, wherein $R_9$ is selected from the group consisting of H, Cl,

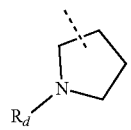

and $C_{1-4}$ alkylamino, and other variables are as defined herein.

In some embodiments of the present invention, provided is the compound, the pharmaceutically acceptable salt thereof or the isomer thereof, wherein $R_9$ is selected from the group consisting of H, Cl,

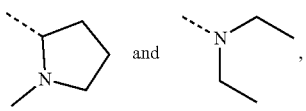

and other variables are as defined herein.

In some embodiments of the present invention, provided is the compound, the pharmaceutically acceptable salt thereof or the isomer thereof, wherein the structural unit

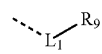

is selected from the group consisting of H, Cl,

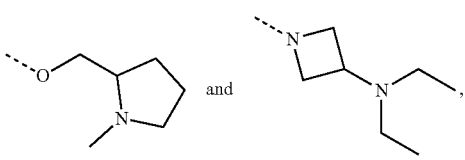

and other variables are as defined herein.

In some embodiments of the present invention, provided is the compound, the pharmaceutically acceptable salt thereof or the isomer thereof, wherein $R_{10}$ is selected from the group consisting of H and

and other variables are as defined herein.

In some embodiments of the present invention, provided is the compound, the pharmaceutically acceptable salt thereof or the isomer thereof, wherein the structural unit -$L_2$-$L_3$-$R_{10}$ is selected from the group consisting of H,

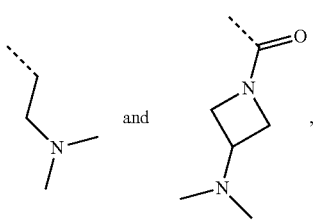

and other variables are as defined herein.

In some embodiments of the present invention, provided is the compound, the pharmaceutically acceptable salt thereof or the isomer thereof, wherein the compound is selected from

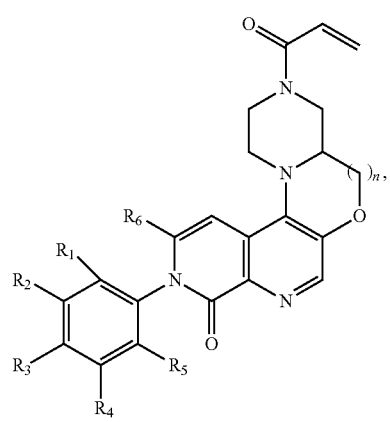

(I)

wherein $R_1$, $R_2$, $R_3$, $R_4$, $R_5$, $R_6$ and n are as defined herein.

The present invention also provides a compound of a formula below, a pharmaceutically acceptable salt thereof or an isomer thereof, selected from the group consisting of

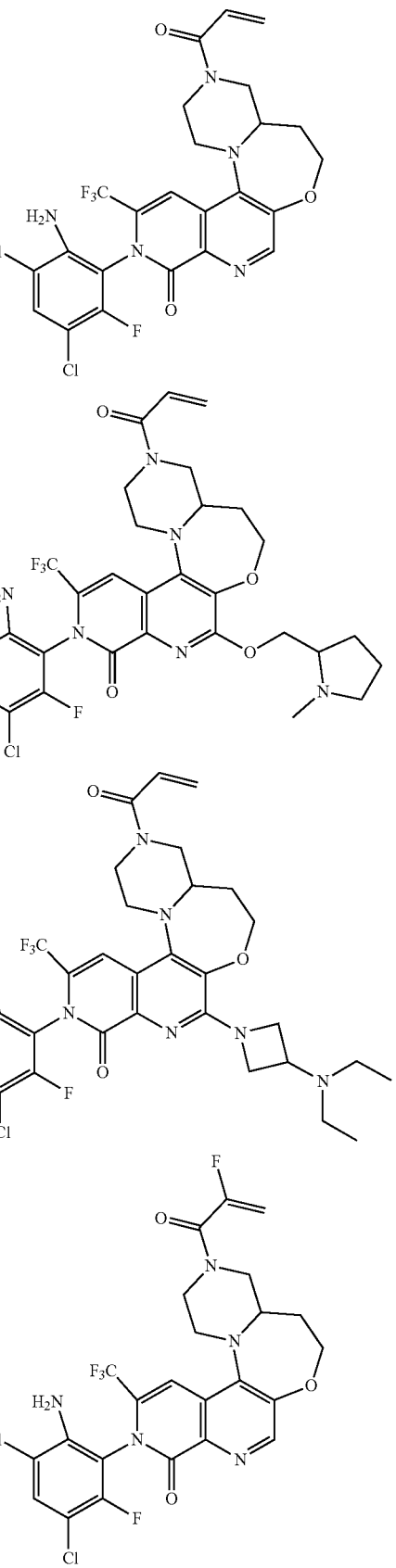

-continued
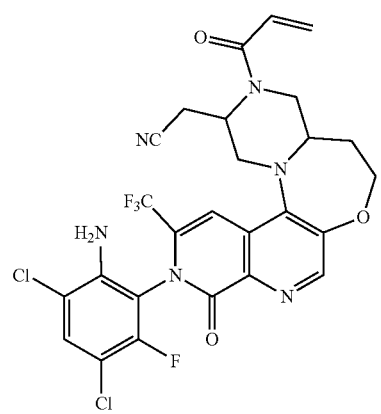
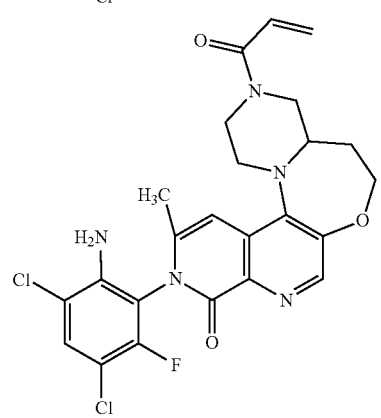
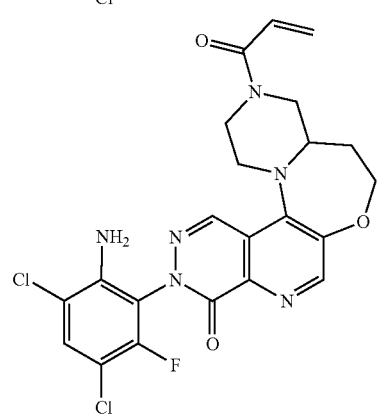
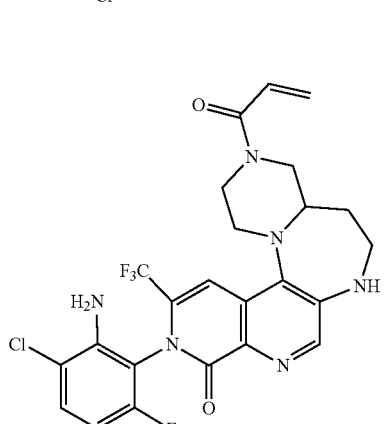
-continued
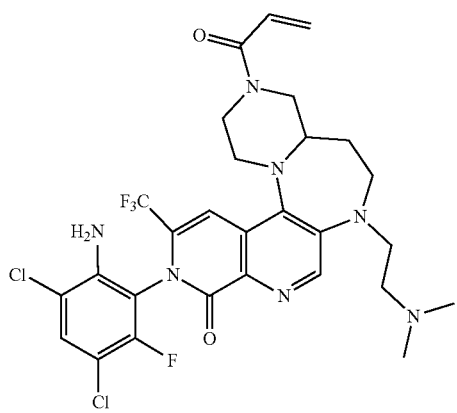
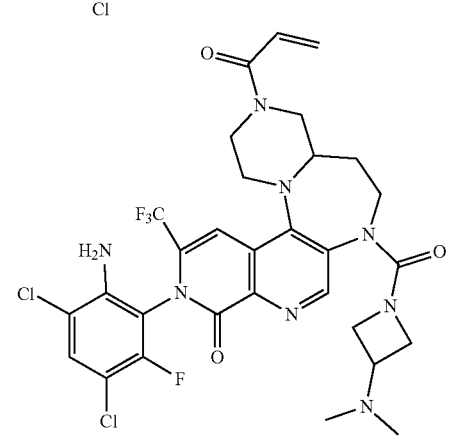
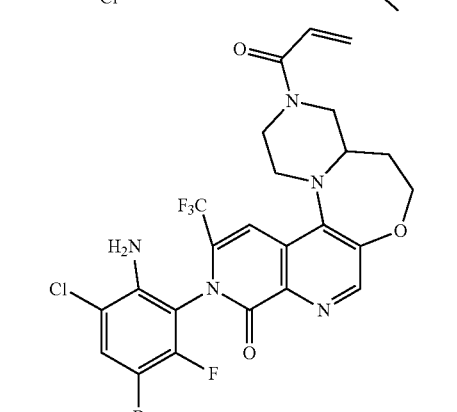
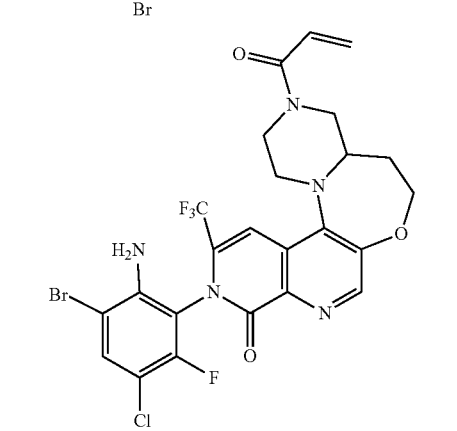

-continued

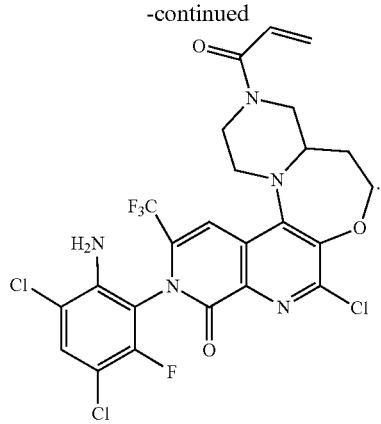

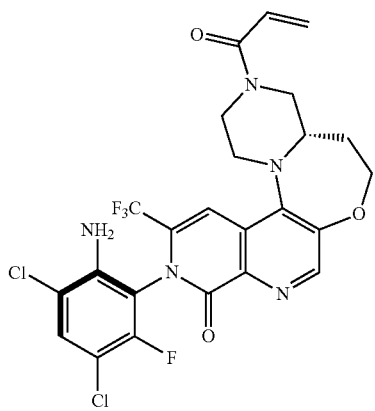

In some embodiments of the present invention, provided is the compound, the pharmaceutically acceptable salt thereof or the isomer thereof, selected from the group consisting of

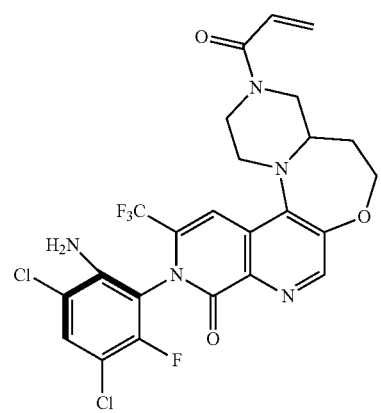

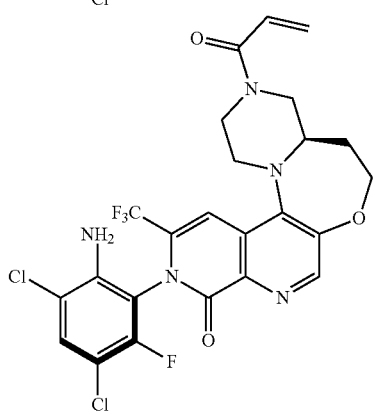

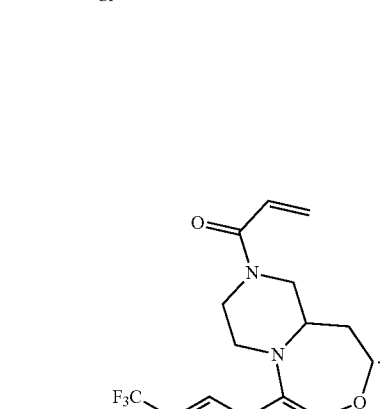

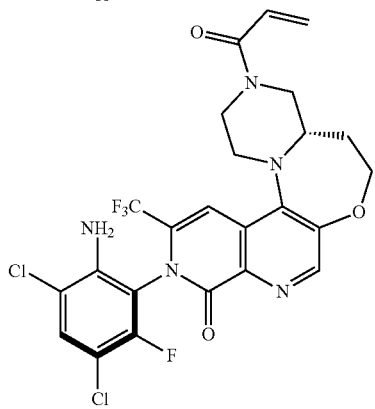

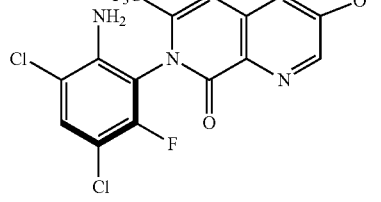

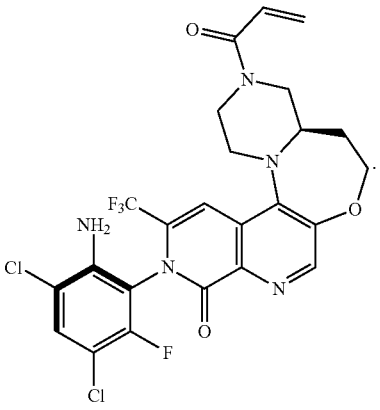

In some embodiments of the present invention, provided is the compound, the pharmaceutically acceptable salt thereof or the isomer thereof, selected from the group consisting of The present invention provides a compound of formula (I), a pharmaceutically acceptable salt thereof or an isomer thereof,

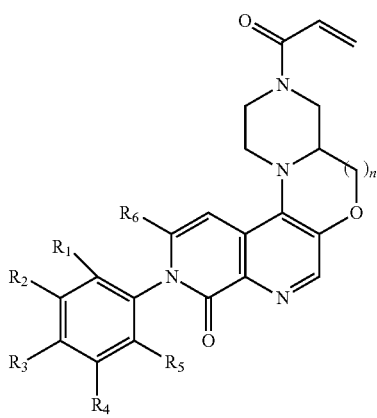

wherein,

- $R_1$ is H, F, Cl, Br, I, $NH_2$ and $C_{1-3}$ alkyl, wherein the $C_{1-3}$ alkyl is optionally substituted with 1, 2 or 3 $R_a$;
- $R_2$, $R_3$, $R_4$ and $R_5$ are each independently selected from the group consisting of H, F, Cl, Br, I and $C_{1-3}$ alkyl, wherein the $C_{1-3}$ alkyl is optionally substituted with 1, 2 or 3 $R_b$;
- $R_6$ is selected from the group consisting of H, F, Cl, Br, I and $C_{1-3}$ alkyl, wherein the $C_{1-3}$ alkyl is optionally substituted with 1, 2 or 3 $R_c$;
- $R_a$, $R_b$ and $R_c$ are each independently selected from the group consisting of H, F, Cl, Br and I; and
- n is selected from 2.

In some embodiments of the present invention, in the formula (I), $R_1$ is selected from $NH_2$, and other variables are as defined herein.

In some embodiments of the present invention, in the formula (I), $R_2$ is selected from Cl, and other variables are as defined herein.

In some embodiments of the present invention, in the formula (I), $R_3$ is selected from H, and other variables are as defined herein.

In some embodiments of the present invention, in the formula (I), $R_4$ is selected from Cl, and other variables are as defined herein.

In some embodiments of the present invention, in the formula (I), $R_5$ is selected from F, and other variables are as defined herein.

In some embodiments of the present invention, in the formula (I), the structural unit

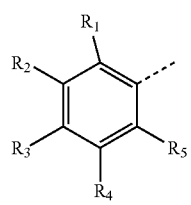

is

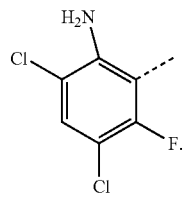

In some embodiments of the present invention, in the formula (I), $R_6$ is selected from the group consisting of H, F, Cl, Br, I, $CH_3$, $CF_3$, $CHF_2$ and $CH_2F$, and other variables are as defined herein.

In some embodiments of the present invention, in the formula (I), $R_6$ is selected from $CF_3$, and other variables are as defined herein.

Still some other embodiments of the present invention are derived from any combination of the variables as described above.

The present invention also provides a compound of a formula below, a pharmaceutically acceptable salt thereof or an isomer thereof, selected from

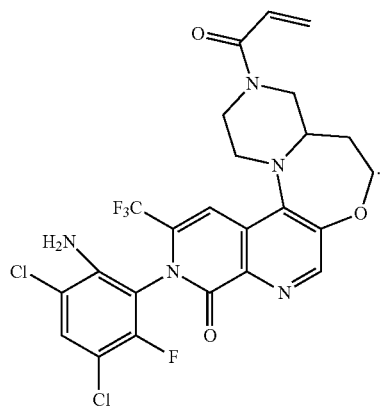 [SMILES: C=CC(=O)N1CCN2c3c(cnc4c(=O)n(-c5c(N)c(Cl)cc(Cl)c5F)c(C(F)(F)F)cc34)OCCC2C1]

Still some other embodiments of the present invention are derived from any combination of the variables as described above.

The present invention provides a pharmaceutical composition comprising a therapeutically effective amount of the compound or the pharmaceutically acceptable salt thereof disclosed herein as an active ingredient, and a pharmaceutically acceptable carrier.

The present invention provides use of the compound, the pharmaceutically acceptable salt thereof or the isomer thereof, or the composition for preparing KRAS G12C mutant protein inhibitors.

The present invention provides use of the compound, the pharmaceutically acceptable salt thereof or the isomer thereof, or the composition for preparing a medicament for the treatment of cancer.

Definitions and Description

Unless otherwise stated, the following terms and phrases used herein are intended to have the following meanings. A particular term or phrase, unless otherwise specifically defined, should not be considered as uncertain or unclear, but construed according to its common meaning. When referring to a trade name, it is intended to refer to its corresponding commercial product or its active ingredient. The term "pharmaceutically acceptable" is used herein for those compounds, materials, compositions and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

The term "pharmaceutically acceptable salt" refers to a salt of the compound disclosed herein, which is prepared from the compound having particular substituents disclosed herein and a relatively nontoxic acid or base. When the compound disclosed herein contains a relatively acidic functional group, a base addition salt can be given by contacting the neutral form of such a compound with a sufficient amount of a base in a pure solution or a suitable inert solvent. Pharmaceutically acceptable base addition salts include sodium, potassium, calcium, ammonium, organic amine, or magnesium salts, or similar salts. When the compound disclosed herein contains a relatively basic functional group, an acid addition salt can be given by contacting the neutral form of such a compound with a sufficient amount of an acid in a pure solution or a suitable inert solvent. Examples of pharmaceutically acceptable acid addition salts include salts derived from inorganic acids, such as hydrochloric acid, hydrobromic acid, nitric acid, carbonic acid, bicarbonate radical, phosphoric acid, monohydrogen phosphate, dihydrogen phosphate, sulfuric acid, hydrogen sulfate, hydroiodic acid and phosphorous acid; and salts derived from organic acids, such as acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid and methanesulfonic acid. Also included are salts of amino acids (e.g., arginine) and salts of organic acids such as glucuronic acid. Certain specific compounds disclosed herein contain both basic and acidic functional groups that allow the compounds to be converted into either base or acid addition salts.

The pharmaceutically acceptable salts disclosed herein can be synthesized from a parent compound having an acidic or basic group by conventional chemical methods. In general, such salts are prepared by the following method: the free acid or base form of the compound reacting with a stoichiometric amount of the appropriate base or acid in water or an organic solvent or a mixture thereof.

In addition to salt forms, the compounds provided herein also exist in prodrug forms. Prodrugs of the compounds described herein readily undergo chemical changes under physiological conditions to convert to the compounds disclosed herein. In addition, prodrugs can be converted to the compounds disclosed herein in vivo by chemical or biochemical methods.

Certain compounds disclosed herein may exist in non-solvated forms or solvated forms, including a hydrate form. In general, the solvated forms are included within the scope of the present invention, as are equivalent non-solvated forms.

The compounds disclosed herein may be present in a specific geometric or stereoisomeric form. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereoisomer enriched mixture, all of which are encompassed within the scope of the present invention. Substituents such as alkyl may have an additional asymmetric carbon atom. All these isomers and mixtures thereof are encompassed within the scope of the present application.

Unless otherwise stated, the term "enantiomer" or "optical isomer" refers to stereoisomers that are mirror images of each other.

Unless otherwise stated, the term "cis-trans isomer" or "geometric isomer" results from the inability of a single bond of a ring carbon atom or a double bond to rotate freely.

Unless otherwise stated, the term "diastereoisomer" refers to stereoisomers whose molecules have two or more chiral centers and are not mirror images of each other.

Unless otherwise stated, "(D)" or "(+)" stands for dextrorotation, "(L)" or "(−)" stands for levorotation, and "(DL)" or "(+)" stands for racemization.

Unless otherwise stated, the absolute configuration of a stereogenic center is represented by a wedged solid bond ( ▰ ) and a wedged dashed bond ( ▱ ), and the relative configuration of a stereogenic center is represented by a straight solid bond ( ▰ ) and a straight dashed bond ( ▱ ). A wavy line ( ∿ ) represent's a wedged solid bond ( ▰ ) or a wedged dashed bond ( ▱ ), or a wavy line ( ∿ ) represents a straight solid bond ( ▰ ) and a straight dashed bond ( ▱ ).

The compounds disclosed herein may be present in a specific tautomeric form. Unless otherwise stated, the term "tautomer" or "tautomeric form" means that different functional isomers are in dynamic equilibrium at room temperature and can be rapidly converted into each other. If tautomers are possible (e.g., in solution), the chemical equilibrium of the tautomers can be achieved. For example, a proton tautomer, also known as a prototropic tautomer, includes the interconversion by proton transfer, such as keto-enol isomerization and imine-enamine isomerization. A valence isomer includes the interconversion by recombination of some bonding electrons. A specific example of the keto-enol tautomerization is the interconversion between two tautomers pentane-2,4-dione and 4-hydroxypent-3-en-2-one.

Unless otherwise stated, the term "rich in one isomer", "isomer-rich", "rich in one enantiomer", or "enantiomer-rich" means that the content of one of the isomers or enantiomers is less than 100% and more than or equal to 60%, 70%, 80%, 90%, 95%, 96%, 97%, 98%, 99%, 99.5%, 99.6%, 99.7%, 99.8% or 99.9%. Unless otherwise stated, the term "isomeric excess" or "enantiomeric excess" refers to the difference between the relative percentages of two isomers or enantiomers. For example, if the content of one isomer or enantiomer is 90% and the content of the other isomer or enantiomer is 10%, the isomeric or enantiomeric excess (ee) is 80%.

Optically active (R)- and (S)-isomers and D and L isomers can be prepared by chiral synthesis or chiral reagents or other conventional techniques. If one enantiomer of a certain compound disclosed herein is to be obtained, the desired pure enantiomer can be prepared by asymmetric synthesis or derivatization using a chiral additive, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods in the art to give the pure enantiomer. Furthermore, the enantiomer and the diastereoisomer are generally isolated through chromatography using a chiral stationary phase, optionally in combination with chemical derivatization (e.g., carbamate generated from amines). The compounds disclosed herein may contain an unnatural proportion of atomic isotope at one or more of the atoms that constitute the compound. For example, the compound may be labeled with a radioisotope, such as tritium ($^3H$), iodine-125 ($^{125}I$), or C-14 ($^{14}C$). For another example, hydrogen can be substituted with deuterium to form a deuterated drug, and the bond formed by deuterium and carbon is firmer than that formed by common hydrogen and carbon. Compared with an undeuterated drug, the deuterated drug has the advantages of reduced toxic side effect, increased stability, enhanced efficacy, prolonged biological half-life and the like. All isotopic variations of the compounds disclosed herein, whether radioactive or not, are encompassed within the scope of the present application. "Optional" or "optionally" means that the subsequently described event or circumstance may, but not necessarily, occur, and the description includes instances where the event or circumstance occurs and instances where it does not.

The term "substituted" means that one or more hydrogen atoms on a specific atom are substituted with substituents which may include deuterium and hydrogen variants, as long as the valence of the specific atom is normal and the substituted compound is stable. When the substituent is an oxygen (i.e., =O), it means that two hydrogen atoms are substituted. Substitution by oxygen does not occur on aromatic groups. The term "optionally substituted" means that an atom can be substituted with a substituent or not. Unless otherwise specified, the type and number of the substituent may be arbitrary as long as being chemically achievable.

When any variable (e.g., R) occurs more than once in the constitution or structure of a compound, the variable is independently defined in each case. Thus, for example, if a group is substituted with 0-2 R, the group can be optionally substituted with two R at most, and the definition of R in each case is independent. Furthermore, a combination of a substituent and/or a variant thereof is permissible only if the combination can result in a stable compound.

When the number of a linking group is 0, for example, —(CRR)$_0$—, it means that the linking group is a single bond.

When one of variants is selected from a single bond, then two groups bonding by this variant are bonded directly. For example, in A-L-Z, when L represents a single bond, it means that the structure is actually A-Z.

When a substituent is absent, it means that the substituent does not exist. For example, when X in A-X is absent, the structure is actually A. When it is not specified by which atom the listed substituent is connected to the group to be substituted, the substituent can be connected via any atom of the group. For example, pyridinyl as a substituent can be connected to the group to be substituted through any carbon atom on the pyridine ring.

When the enumerative linking group does not indicate the direction for linking, the direction for linking is arbitrary. For example, when the linking group L contained in

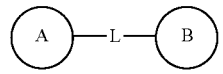

is -M-W—, -M-W— can either link ring A and ring B in a direction same as left-to-right reading order to form

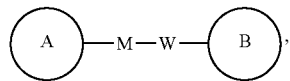

or link ring A and ring B in an opposing direction to form

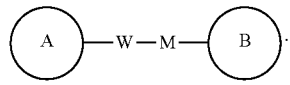

A combination of the linking group, a substituent and/or a variant thereof is permissible only if the combination can result in a stable compound.

Unless otherwise specified, the term "$C_{1-3}$ alkyl" refers to a linear or branched saturated hydrocarbon group consisting of 1 to 3 carbon atoms. The $C_{1-3}$ alkyl includes, but is not limited to, $C_{1-2}$ and $C_{2-3}$ alkyl, etc., and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), and the like.

Unless otherwise specified, the term "$C_{1-6}$ alkylamino" refers to an alkyl group containing 1 to 6 carbon atoms that is attached to the rest of the molecule through an amino group. The $C_{1-6}$ alkylamino includes $C_{1-4}$, $C_{1-3}$, $C_{1-2}$, $C_{2-6}$, $C_{2-4}$, $C_6$, $C_5$, $C_4$, $C_3$, $C_2$ alkylamino and the like. Examples of $C_{1-6}$ alkylamino include, but are not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, and the like.

Unless otherwise specified, the term "$C_{1-4}$ alkylamino" refers to an alkyl group containing 1 to 4 carbon atoms that is attached to the rest of the molecule through an amino group. The $C_{1-4}$ alkylamino group includes $C_{1-3}$ alkylamino, $C_{1-2}$ alkylamino, $C_{2-4}$ alkylamino, $C_4$ alkylamino, $C_3$ alkylamino, $C_2$ alkylamino, and the like. Examples of $C_{1-4}$ alkylamino include, but are not limited to, —NHCH$_3$, —N(CH$_3$)$_2$, —NHCH$_2$CH$_3$, —N(CH$_3$)CH$_2$CH$_3$, —N(CH$_2$CH$_3$)(CH$_2$CH$_3$), —NHCH$_2$CH$_2$CH$_3$, —NHCH$_2$(CH$_3$)$_2$, —NHCH$_2$CH$_2$CH$_2$CH$_3$, and the like.

Unless otherwise specified, $C_{n-n+m}$ or $C_n$-$C_{n+m}$ includes any one of the specific cases of n to n+m carbon atoms. For example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$. Also, any range within n to n+m may be included. For example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc. Similarly, n–n+m membered represents that the number of atoms on the ring is n to n+m. For example, 3-12 membered ring includes 3 membered ring, 4 membered ring, 5 membered ring, 6 membered ring, 7 membered ring, 8 membered ring, 9 membered ring, 10 membered ring, 11 membered ring and 12 membered ring. n–n+m membered also represents any range within n to n+m. For example, 3-12 membered ring includes 3-6 membered ring, 3-9 membered ring, 5-6 membered ring, 5-7 membered ring, 6-7 membered ring, 6-8 membered ring, 6-10 membered ring, etc.

The term "leaving group" refers to a functional group or atom that can be replaced by another functional group or atom through a substitution reaction (e.g., nucleophilic substitution). For example, representative leaving groups include triflate; chlorine, bromine and iodine; sulfonate groups, such as mesylate, tosylate, p-bromobenzenesulfonate, and p-toluenesulfonate; and acyloxy groups, such as acetoxy and trifluoroacetoxy.

The term "protecting group" includes, but is not limited to, "amino protecting group", "hydroxy protecting group" or "sulfydryl protecting group". The term "amino protecting group" refers to a protecting group suitable for preventing side reactions at the nitrogen atom of the amino. Representative amino protecting groups include, but are not limited to: formyl; acyl, such as alkanoyl (such as acetyl, trichloroacetyl or trifluoroacetyl); alkoxycarbonyl, such as tert-butoxycarbonyl (Boc); arylmethoxycarbonyl, such as carbobenzoxy (Cbz) and 9-fluorenylmethoxycarbonyl (Fmoc); arylmethyl, such as benzyl (Bn), trityl(Tr), 1,1-di-(4'-methoxyphenyl)methyl; and silyl, such as trimethylsilyl (TMS) and tert-butyldimethylsilyl (TBS).

The term "hydroxyl protecting group" refers to a protecting group suitable for preventing side reactions of the hydroxyl group. Representative hydroxy protecting groups include, but are not limited to: alkyl, such as methyl, ethyl, and tert-butyl; acyl, such as alkanoyl (such as acetyl); arylmethyl, such as benzyl (Bn), p-methoxybenzyl (PMB), 9-fluorenylmethyl(Fm) and diphenylmethyl (DPM); and silyl, such as trimethylsilyl (TMS) and tert-butyldimethylsilyl (TBS).

The compounds disclosed herein can be prepared by a variety of synthetic methods well known to those skilled in the art, including the specific examples listed below, examples formed by combinations thereof with other chemical synthetic methods, and equivalents thereof known to those skilled in the art. Preferred examples include, but are not limited to, the examples of the present invention.

The solvent used in the present invention can be commercially available.

Compounds are named according to conventional nomenclature rules in the art or using ChemDraw® software, and supplier's catalog names are given for commercially available compounds.

Technical Effects

The compounds disclosed herein are superior KRAS G12C mutant protein inhibitor. Compounds 1-11A and 1-11D disclosed herein show higher anti-proliferative activity against KRAS G12C mutant cells NCI-H358, and weaker anti-proliferative activity against wild type A375 cells, thereby showing high selectivity. In the pharmacokinetic evaluation experiment of mice, compound 1-11A disclosed herein shows high exposure and oral bioavailability. Compound 1-11A disclosed herein exhibits good in vivo efficacy in an NCI-H358 subcutaneous xenograft tumor model of human non-small cell lung cancer. At the dose of 3 mg/kg, 1-11A has a strong tumor growth inhibition effect, while at the increased dose of 10 mg/kg, 1-11A shows a stronger tumor inhibition effect than that at 3 mg/kg, with the tumor growth inhibition rate up to 83.9%.

DETAILED DESCRIPTION

The present invention is described in detail below by way of examples. However, this is by no means disadvantageously limiting the scope of the present invention. The compounds disclosed herein can be prepared by a variety of synthetic methods well known to those skilled in the art, including the specific examples listed below, examples formed by combinations thereof with other chemical synthetic methods, and equivalents thereof known to those skilled in the art. Preferred examples include, but are not limited to, the examples of the present invention. It will be apparent to those skilled in the art that various changes and modifications can be made to the specific examples of the present invention without departing from the spirit and scope of the present invention.

Example 1. Preparation of Compounds 1-11A, 1-11B, 1-11C and 1-11D

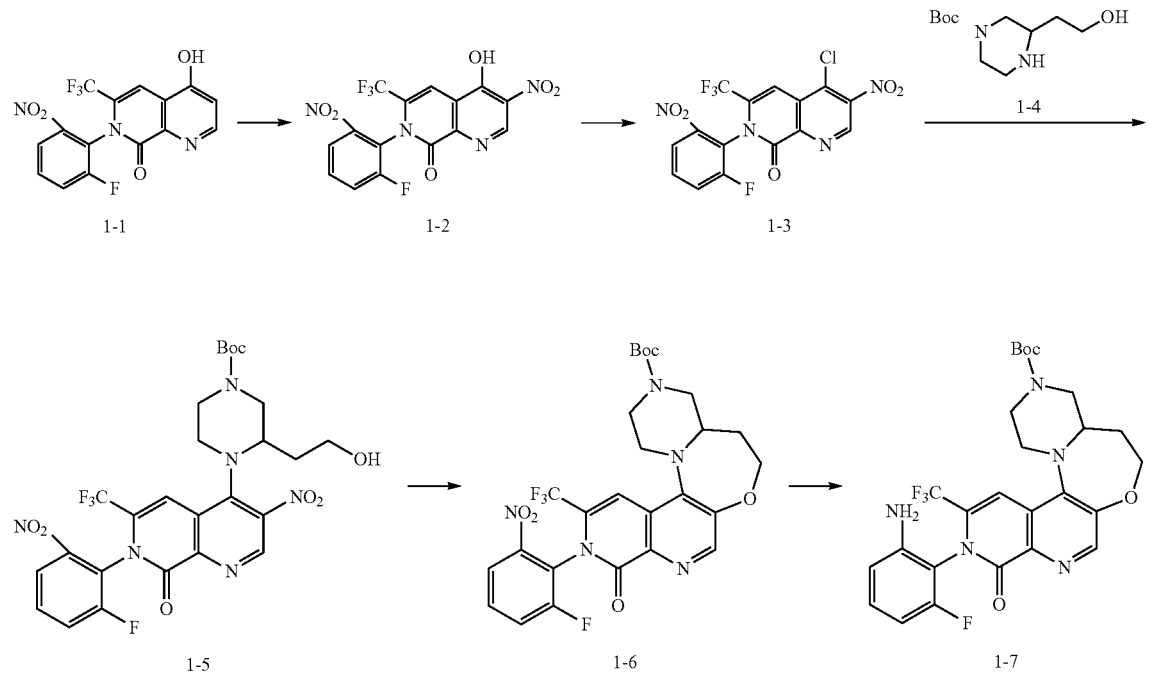

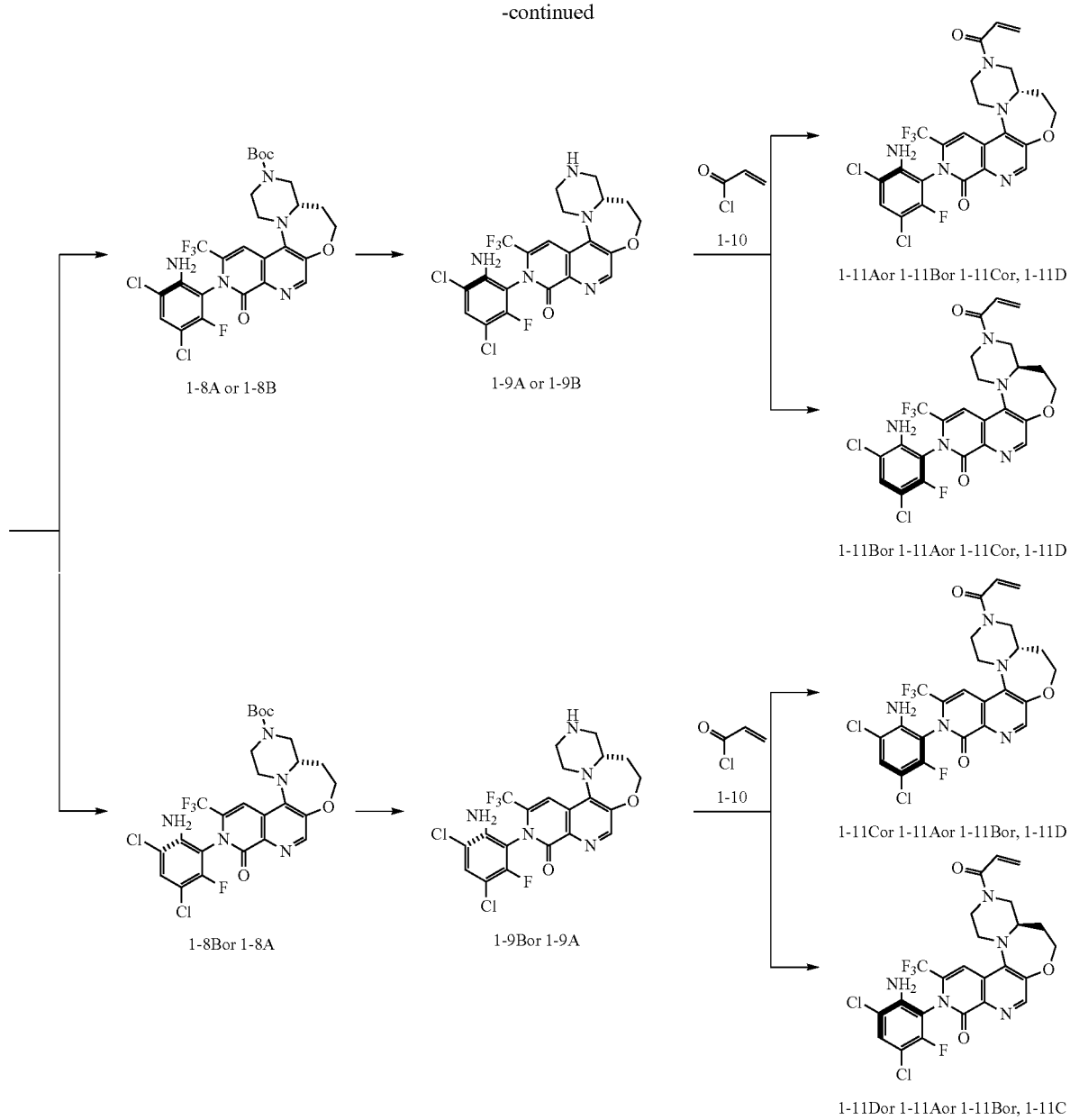

Step 1.

A solution of compound 1-1 (5.0 g, 13.54 mmol, 1.0 eq) in propionic acid (50 mL) was heated to 125° C., followed by the slow addition of fuming nitric acid (2.56 g, 40.63 mmol, 1.83 mL, 3.0 eq). The reaction solution was reacted at 125° C. for 2 h. The reaction solution was slowly poured into 10 wt % ice brine (100 mL), and filtered. The filter cake was dried to give compound 1-2. $^{1}$H NMR (400 MHz, DMSO-$d_6$) δ 8.86 (s, 1H), 8.35 (d, J=8.31 Hz, 1H), 8.11-8.19 (m, 1H), 8.02-8.10 (m, 1H), 7.61 (s, 1H). LCMS (ESI) m/z: 415.0 (m+1)$^{+}$.

Step 2.

A solution of compound 1-2 (2.5 g, 6.04 mmol, 1.0 eq) in phosphorus oxychloride (41.25 g, 269.02 mmol, 25 mL, 44.57 eq) was heated to 100° C., followed by the addition of N,N-dimethylaniline (731.37 mg, 6.04 mmol, 765.03 μL, 1.0 eq). The reaction mixture was stirred at 100° C. for 30 min, and distilled under reduced pressure to remove the solvent. The resulting residue was diluted with ethyl acetate (20 mL) and slowly added to ice water (50 mL), and the mixture was extracted with ethyl acetate (50 mL×2). The organic phases were combined, washed with saturated brine (50 mL×2), dried over anhydrous sodium sulfate, filtered and concentrated under reduced pressure to give compound 1-3. LCMS (ESI) m/z: 433.0 (m+1)$^{+}$.

Step 3.

To a solution of compound 1-3 (500 mg, 1.16 mmol, 1.0 eq) in dimethyl sulfoxide (5 mL) were added diisopropylethylamine (448.05 mg, 3.47 mmol, 603.85 μL, 3.0 eq) and compound 1-4 (532.28 mg, 2.31 mmol, 2.0 eq). The reaction solution was purged three times with nitrogen and reacted at 25° C. for 16 h. To the reaction solution was added room-temperature water (50 mL), and the resulting mixture was extracted with ethyl acetate (50 mL×3). The organic phases were combined, washed with saturated brine (50 mL×2), dried over anhydrous sodium sulfate, filtered and concentrated under reduced pressure. The resulting residue was purified by silica gel chromatography (petroleum ether:ethyl acetate=2:1 to dichloromethane:methanol=20:1) to give compound 1-5. LCMS (ESI) m/z: 627.2 (m+1)$^+$.

Step 4.

To a solution of compound 1-5 (360 mg, 574.61 mmol, 1.0 eq) in N,N-dimethylformamide (36 mL) was added potassium carbonate (158.83 mg, 1.15 mmol, 2.0 eq). The reaction solution was reacted in an oil bath at 120° C. for 14 h. To the reaction solution was added room-temperature water (50 mL), and the resulting mixture was extracted with ethyl acetate (50 mL×2). The organic phases were combined, washed with saturated brine (50 mL×2) and concentrated under reduced pressure. The resulting residue was purified by silica gel chromatography (petroleum ether:ethyl acetate=1:1) to give compound 1-6. $^1$H NMR (400 MHz, CDCl$_3$-d) δ 8.52 (d, J=1.00 Hz, 1H), 8.13-8.23 (m, 1H), 7.73 (dt, J$_1$=8.41 Hz, J$_2$=5.27 Hz, 1H), 7.57-7.67 (m, 1H), 7.20 (d, J=5.52 Hz, 1H), 4.57 (br d, J=0.90 Hz, 1H), 4.10-4.19 (m, 2H), 3.80 (br s, 1H), 3.22-3.49 (m, 4H), 2.78-2.93 (m, 1H), 2.18-2.46 (m, 2H), 1.51 (s, 9H). LCMS (ESI) m/z: 580.3 (m+1)$^+$.

Step 5.

To a mixed solution of compound 1-6 (200 mg, 342.30 mmol, 1.0 eq) in ethanol (5 mL) and water (2.5 mL) were added iron powder (95.58 mg, 1.71 mmol, 5.0 eq) and ammonium chloride (91.55 mg, 1.71 mmol, 5.0 eq). The reaction solution was reacted in an oil bath at 80° C. for 2 h. The reaction solution was filtered and the filter cake was washed with ethanol (20 mL). The filtrate was concentrated under reduced pressure. The resulting residue was diluted with ethyl acetate (20 mL), washed with room-temperature water (20 mL) and saturated brine (20 mL), dried over anhydrous sodium sulfate, filtered and concentrated under reduced pressure to give compound 1-7. $^1$H NMR (400 MHz, CDCl$_3$-d) δ 8.48-8.55 (m, 1H), 7.15-7.26 (m, 2H), 6.55-6.68 (m, 2H), 4.50-4.63 (m, 1H), 4.27-4.37 (m, 1H), 3.71-3.88 (m, 3H), 3.22-3.49 (m, 4H), 2.33-2.45 (m, 1H), 2.14-2.26 (m, 1H), 1.51 (s, 9H). LCMS (ESI) m/z: 550.3 (m+3). LCMS (ESI) m/z: 550.3 (m+1)$^+$.

Step 6.

To a solution of compound 1-7 (300 mg, 545.93 mmol, 1.0 eq) in acetonitrile (6 mL) was added chlorosuccinimide (138.51 mg, 1.04 mmol, 1.9 eq) at 0° C. The reaction solution was reacted in an oil bath at 60° C. for 2 h. The reaction solution was slowly added to a saturated sodium sulfite solution (20 mL), and the resulting mixture was extracted with ethyl acetate (20 mL×2). The organic phases were combined, washed with saturated brine (20 mL×2), dried over anhydrous sodium sulfate, filtered and concentrated under reduced pressure. The resulting residue was purified by silica gel chromatography (petroleum ether:ethyl acetate=2:1) to give compounds 1-8A and 1-8B. LCMS (ESI) m/z: 618.2 (m+1)$^+$.

Step 7.

To a solution of compound 1-8A (Rf=0.5) (70 mg, 113.19 mmol, 1.0 eq) in ethyl acetate (0.5 mL) was added hydrogen chloride in ethyl acetate (4 mol/L, 0.5 mL, 17.67 eq). The reaction solution was reacted at 25° C. for 1 h. The reaction solution was concentrated under reduced pressure to give compound 1-9A hydrochloride. LCMS (ESI) m/z: 518.1 (m+1)$^+$.

Step 8.

To a solution of compound 1-9A (62 mg, 111.76 mmol, 1.0 eq, hydrochloride) in dichloromethane (2 mL) were added diisopropylethylamine (72.22 mg, 558.81 mmol, 97.33 µL, 5.0 eq) and compound 1-10 (11.13 mg, 122.94 mmol, 10.02 µL, 1.1 eq) at 0° C. The reaction solution was reacted at 0° C. for 0.5 h. To the reaction solution was added saturated ammonium chloride (10 mL), and the resulting mixture was extracted with ethyl acetate (10 mL×2). The organic phases were combined and concentrated under reduced pressure. The resulting residue was purified by preparative HPLC (mobile phase: water (10 mmol ammonium bicarbonate)-acetonitrile, gradient: acetonitrile 31%-61%, 10 min). The resulting product was purified by preparative SFC (column model: DAICEL CHIRALPAK AD (250 mm×30 mm, 10 µm), mobile phase: isopropanol (0.1% ammonium hydroxide), gradient: carbon dioxide critical fluid 40%-40%, 4.8 min, 35 min) to give compounds 1-11A (rt=0.953 min) and 1-11B (rt=1.264 min). 1-11A: $^1$H NMR (400 MHz, MeOH-d$_4$) δ 8.41 (s, 1H), 7.53 (d, J=7.38 Hz, 1H), 7.33 (s, 1H), 6.74-6.96 (m, 1H), 6.28 (br d, J=17.26 Hz, 1H), 5.82 (dd, J$_1$=10.63 Hz, J$_2$=1.75 Hz, 1H), 4.55 (br d, J=3.13 Hz, 1H), 4.24 (br s, 2H), 3.82-4.07 (m, 2H), 3.72 (br s, 1H), 3.45-3.51 (m, 1H), 3.38 (br d, J=10.76 Hz, 2H), 2.17-2.37 (m, 2H); LCMS (ESI) m/z: 572.0 (m+1)$^+$. 1-11B: $^1$H NMR (400 MHz, MeOH-d$_4$) δ 8.41 (s, 1H), 7.53 (d, J=7.38 Hz, 1H), 7.33 (s, 1H), 6.75-6.97 (m, 1H), 6.28 (br d, J=17.13 Hz, 1H), 5.82 (dd, J$_1$=10.63 Hz, J$_2$=1.75 Hz, 1H), 4.54 (br d, J=6.13 Hz, 1H), 4.17-4.39 (m, 2H), 3.83-4.08 (m, 2H), 3.72 (br s, 1H), 3.45-3.51 (m, 1H), 3.38 (br d, J=11.63 Hz, 2H), 2.16-2.35 (m, 2H); LCMS (ESI) m/z: 572.0 (m+1)$^+$.

Step 9.

To a solution of compound 1-8B (Rf=0.4) (80 mg, 129.36 mmol, 1.0 eq) in ethyl acetate (0.5 mL) was added hydrogen chloride in ethyl acetate (4 mol/L, 0.5 mL, 15.46 eq). The reaction solution was reacted at 25° C. for 1 h. The reaction solution was concentrated under reduced pressure to give compound 1-9B hydrochloride.

LCMS (ESI) m/z: 518.1 (m+1)$^+$.

Step 10.

To a solution of compound 1-9B (71 mg, 127.99 mmol, 1.0 eq, hydrochloride) in dichloromethane (2 mL) were added diisopropylethylamine (82.71 mg, 639.93 mmol, 111.46 µL, 5.0 eq) and compound 1-10 (12.74 mg, 140.78 mmol, 11.48 µL, 1.1 eq) at 0° C. The reaction solution was reacted at 0° C. for 0.5 h. To the reaction solution was added saturated ammonium chloride (10 mL), and the resulting mixture was extracted with ethyl acetate (10 mL×2). The organic phases were combined and concentrated under reduced pressure. The resulting residue was purified by preparative HPLC (mobile phase: water (10 mmol ammonium bicarbonate)-acetonitrile, gradient: acetonitrile 30%-63%, 11 min). The resulting product was purified by preparative SFC (DAICEL CHIRALPAK AD (250 mm×30 mm, 10 m), mobile phase: isopropanol (0.1% ammonium hydroxide), gradient: carbon dioxide critical fluid 50%-50%, 3.2 min, 40 min) to give compounds 1-11C (rt=0.632 min) and 1-11D (rt=1.519 min).

1-11C: $^1$H NMR (400 MHz, MeOH-d$_4$) δ 8.41 (s, 1H), 7.53 (d, J=7.38 Hz, 1H), 7.35 (br s, 1H), 6.75-6.98 (m, 1H), 6.29 (br dd, J$_1$=17.26 Hz, J$_2$=6.50 Hz, 1H), 5.82 (br d, J=10.63 Hz, 1H), 4.56 (br d, J=12.51 Hz, 1H), 4.01-4.29 (m, 2H), 3.95 (br d, J=6.88 Hz, 2H), 3.76 (br s, 1H), 3.48 (br d, J=12.51 Hz, 1H), 3.34-3.42 (m, 2H), 2.18-2.38 (m, 2H); LCMS (ESI) m/z: 572.0 (m+1)$^+$.

1-11D: $^1$H NMR (400 MHz, MeOH-d$_4$) δ 8.40 (s, 1H), 7.53 (d, J=7.34 Hz, 1H), 7.34 (s, 1H), 6.72-6.99 (m, 1H), 6.29 (br dd, J$_1$=16.81 Hz, J$_2$=5.20 Hz, 1H), 5.82 (br d, J=10.64 Hz, 1H), 4.32-4.71 (m, 3H), 4.21 (br s, 1H), 3.95 (br s, 1H), 3.74 (br d, J=11.49 Hz, 1H), 3.47 (br d, J=12.72 Hz, 1H), 3.35 (br s, 2H), 2.26 (br d, J=7.09 Hz, 2H); LCMS (ESI) m/z: 572.0 (m+1)$^+$.

Experimental Example 1. Cell Assay

Objective:

This experiment was conducted to verify the proliferation inhibitory effect of the compounds disclosed herein on KRAS G12C mutant NCI-H358 human non-small cell lung cancer cells and wild-type A375 human malignant melanoma cells.

Materials:

Cell line NCI-H358 (purchased from the Cell Bank of the Chinese Academy of Sciences), cell line A375 (purchased from the Cell Bank of the Chinese Academy of Sciences), DMEM medium, penicillin/streptomycin antibiotics purchased from Wisent, and fetal calf serum purchased from Biosera. CellTiter-Glo (chemiluminescence detection reagent for cell viability) reagent purchased from Promega.

Method:

1) Anti-Proliferation Experiment on NCI-H358 Cells:

NCI-H358 cells were seeded in a white 96-well plate, with 80 µL of cell suspension containing 4000 NCI-H358 cells added to each well. The cell plate was incubated in a $CO_2$ incubator overnight. The test compounds were serially diluted in a 3-fold gradient with a pipettor to 9th concentration, i.e. from 2 mM to 304 nM, and the duplicate wells were set up. 78 µL of medium was added to an intermediate plate, and the serially diluted compound was transferred to corresponding wells of the intermediate plate at 2 µL/well. After mixing, the mixture was transferred to the cell plate at 20 µL per well. The concentration of the compound transferred to the cell plate ranged from 10 µM to 1.52 nM. The cell plate was incubated in a $CO_2$ incubator for 5 days. Another cell plate was read for signal values on the day of compound addition, and these values were used as the maximum values (the Max value in the equation below) in data analysis. To the cell plate was added the chemiluminescence detection reagent for cell viability at 25 µL/well, and the resulting plate was incubated at room temperature for 10 min to stabilize the luminescence signals. Readings were taken using a multi-marker analyzer. To the cell plate was added the chemiluminescence detection reagent for cell viability at 25 µL/well, and the resulting plate was incubated at room temperature for 10 min to stabilize the luminescence signals. Readings were taken using a multi-marker analyzer.

2) Anti-Proliferation Experiment on A375 Cells:

A375 cells were seeded in a white 96-well plate, with 80 µL of cell suspension containing 2000 A375 cells added to each well. The cell plate was incubated in a $CO_2$ incubator overnight. The test compounds were serially diluted in a 3-fold gradient with a pipettor to 9th concentration, i.e. from 2 mM to 304 nM, and the duplicate wells were set up. 78 µL of medium was added to an intermediate plate, and the serially diluted compound was transferred to corresponding wells of the intermediate plate at 2 µL/well. After mixing, the mixture was transferred to the cell plate at 20 µL per well. The concentration of the compound transferred to the cell plate ranged from 10 µM to 1.52 nM. The cell plate was incubated in a $CO_2$ incubator for 5 days. Another cell plate was read for signal values on the day of compound addition, and these values were used as the maximum values (the Max value in the equation below) in data analysis. To the cell plate was added the chemiluminescence detection reagent for cell viability at 25 Lt/well, and the resulting plate was incubated at room temperature for 10 min to stabilize the luminescence signals. Readings were taken using a multi-marker analyzer. To the cell plate was added the chemiluminescence detection reagent for cell viability at 25 Lt/well, and the resulting plate was incubated at room temperature for 10 min to stabilize the luminescence signals. Readings were taken using a multi-marker analyzer.

Data analysis: the original data were converted to inhibition rate using the equation (Sample−Min)/(Max−Min)×100%, and the $IC_{50}$ value was then curve fitted using four parameters (obtained from the "log(inhibitor) vs. response—Variable slope" model in GraphPad Prism).

Results: $IC_{50}$ data for the anti-proliferative activity of the compounds disclosed herein against NCI-H358 (G12C mutant) and A375 (wild-type) cells are shown in Table 1.

Conclusion: compounds 1-11A and 1-11D disclosed herein show higher cell anti-proliferative activity against KRAS G12C mutant cells NCI-H358, and weaker anti-proliferative activity against wild type A375 cells, thereby showing high selectivity.

TABLE 1

| Test compound | NCI-H358 $IC_{50}$ (µM) | A375 $IC_{50}$ (µM) |
|---|---|---|
| 1-11A | 0.10 | 6.12 |
| 1-11B | 5.03 | >10 |
| 1-11C | 3.58 | 4.78 |
| 1-11D | 0.33 | >10 |

Experimental Example 2. Pharmacokinetic Evaluation on Mice

Objective:

To determine the drug concentration in the plasma of the test animals (male CD-1 mice) at different time points after intravenous and intragastric administration of the test compounds by an LC/MS/MS method. To investigate the pharmacokinetic performance of the test compounds in mice and to evaluate the pharmacokinetic characteristics.

Experimental scheme: test animals: 8 healthy adult male SD rats, divided into 4 groups, 2 in IV group (two groups) and 2 in PO group (two groups), according to the principle of similar body weight. The mice were purchased from Beijing Vital River Laboratory Animal Technology Co., Ltd.

Drug Preparation:

IV group: an appropriate amount of sample was weighed, and an appropriate amount of DMSO, PEG400 and water was sequentially added in the volume ratio of 10:60:30, and the mixture was stirred and ultrasonicated to a clear state (1.5 mg/mL).

PO group: an appropriate amount of sample was weighed, and an appropriate amount of DMSO, PEG400 and water was sequentially added in the volume ratio of 10:60:30, and the mixture was stirred and ultrasonicated to a clear state (1.0 mg/mL).

Administration:

The mice in IV group were each subjected to intravenous administration at a volume of 2 mL/kg and a dose of 3 mg/kg; after fasting overnight, the mice in PO group were each subjected to intragastric administration at a volume of 10 mL/kg and a dose of 10 mg/kg.

Procedures:

For IV group, 30 µL of blood was collected from the male SD rats at 0.0833 h, 0.25 h, 0.5 h, 1 h, 2 h, 4 h, 8 h and 24 h post-dose, and placed in a commercial anticoagulation tube with EDTA-$K_2$ added in advance. For PO group, 200 µL of blood was collected from the male SD rats at 0.25 h, 0.5 h, 1 h, 2 h, 4 h, 8 h, 12 h and 24 h post-dose, and placed in a commercial anticoagulation tube with EDTA-K$_2$ added in advance. The tubes were centrifuged for 15 min to separate the plasma and stored at −60° C. The animals were given free access to food 2 h after the administration. LC/MS/MS method was used to determine the content of the test compounds in the plasma of rats after intravenous and intragastric administration. The linear range of the method was 2.00-6000 nM; plasma samples were analyzed after treatment with acetonitrile to precipitate proteins.

Results: see Table 2.

Conclusion: in the pharmacokinetic evaluation experiment of mice, compound 1-11A disclosed herein shows high exposure and oral bioavailability.

TABLE 2

| Groups | | I-11A |
|---|---|---|
| IV (3 mg/kg) | Cl (mL/Kg/min) | 15.2 |
| | V$_d$ (L/kg) | 1.45 |
| | AUC (nM · h) | 5699 |
| | T$_{1/2}$ (h) | 1.15 |
| PO (10 mg/kg) | C$_{max}$ (nM) | 1700 |
| | T$_{max}$ (h) | 0.50 |
| | AUC (nM · h) | 8481 |
| | F (%) | 47.5 |

Note:
Cl: clearance rate;
V$_d$: volume of distribution;
AUC: exposure;
t$_{1/2}$: half-life;
C$_{max}$: maximum compound concentration after oral administration;
T$_{max}$: time to C$_{max}$;
F: bioavailability.

Experimental Example 3. In Vivo Efficacy Study

Objective:

To evaluate the in vivo efficacy of test compounds in an NCI-H358 subcutaneous xenograft tumor model of human non-small cell lung cancer.

Procedures:

BALB/c nude mice, female, 6-8 weeks old, weighing 18-21 g, 96 in total, provided by Shanghai Lingchang Biotechnology Co., Ltd. NCI-H358 tumor cells were resuspended in PBS to obtain 0.1 mL (5×10$^6$ cells) of cell suspension and inoculated subcutaneously in the right back (5×10$^6$/mouse) of each mouse for tumor growth. The mice were randomly grouped and subjected to intragastric administration once daily when the mean tumor volume reached approximately 150-200 mm$^3$, and the dosages were shown in Table 3. Tumor diameters were measured twice weekly using a vernier caliper. The tumor volume was calculated according to the formula: V=0.5a×b$^2$, where a and b represent the long diameter and short diameter of the tumor, respectively. The efficacy of compounds against tumor was evaluated by TGI (%). TGI (%) refers to the tumor growth inhibition rate. TGI (%)=[(1−(mean tumor volume at the end of administration of a treatment group−mean tumor volume at the start of administration of the treatment group))/(mean tumor volume at the end of treatment of the solvent control group−mean tumor volume at the start of treatment of the solvent control group)]×100%.

Results: see Table 3.

TABLE 3

| Groups | Tumor volume (mm$^3$) (day 20) | TGI (%) |
|---|---|---|
| Solvent control group | 634 | — |
| 1-11A 3 mg/kg (0-20 days) | 332 | 64.1 |
| 1-11A 10 mg/kg (0-20 days) | 240 | 83.9 |

Conclusion:

Compound 1-11A disclosed herein exhibits good in vivo efficacy in an NCI-H358 subcutaneous xenograft tumor model of human non-small cell lung cancer. At the dose of 3 mg/kg, 1-11A has a strong tumor growth inhibitory effect, while at the increased dose of 10 mg/kg, 1-11A shows a stronger tumor growth inhibitory effect than that at 3 mg/kg, with the tumor growth inhibition rate up to 83.9%.

The invention claimed is:

1. A compound of formula (II), a pharmaceutically acceptable salt thereof or a stereoisomer or tautomer thereof,

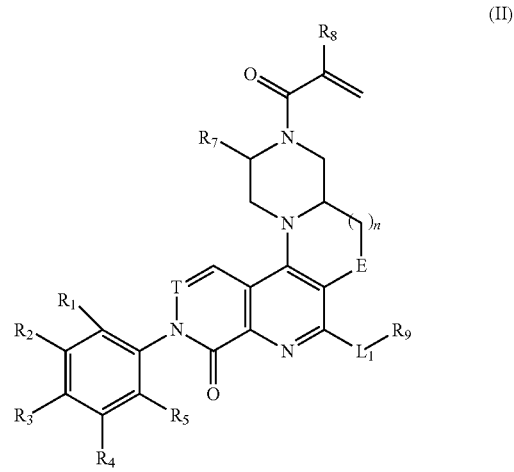

wherein,
R$_1$ is selected from the group consisting of H, F, Cl, Br, I, NH$_2$ and C$_{1-3}$ alkyl, wherein the C$_{1-3}$ alkyl is optionally substituted with 1, 2 or 3 R$_a$;
R$_2$, R$_3$, R$_4$ and R$_5$ are each independently selected from the group consisting of H, F, Cl, Br, I and C$_{1-3}$ alkyl, wherein the C$_{1-3}$ alkyl is optionally substituted with 1, 2 or 3 R$_b$;
T is selected from the group consisting of C (R$_6$) and N;
R$_6$ is selected from the group consisting of H, F, Cl, Br, I and C$_{1-3}$ alkyl, wherein the C$_{1-3}$ alkyl is optionally substituted with 1, 2 or 3 R$_c$;
R$_7$ is selected from the group consisting of H and —CH$_2$—CN;
R$_8$ is selected from the group consisting of H and F;
L$_1$ is selected from the group consisting of a single bond,

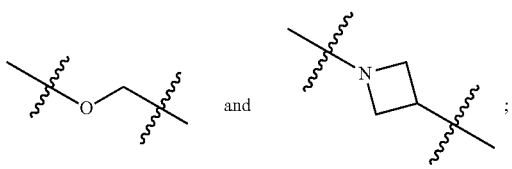

R₉ is selected from the group consisting of H, Cl, pyrrolidinyl and C₁₋₆ alkylamino, wherein the pyrrolidinyl and the C₁₋₆ alkylamino are optionally substituted with 1, 2 or 3 R_d;

E is selected from the group consisting of —O— and —N-(L₂-L₃-R₁₀);

L₂ is selected from the group consisting of a single bond, —CH₂— and —C(=O)—;

L₃ is selected from the group consisting of a single bond, —CH₂— and

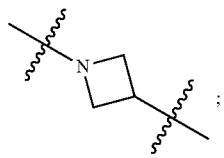 [SMILES: *C1CN(*)C1]
;

R₁₀ is selected from the group consisting of H and C₁₋₆ alkylamino;

R_a, R_b, R_c and R_d are each independently selected from the group consisting of H, F, Cl, Br, I and CH₃; and n is selected from 2.

2. The compound, the pharmaceutically acceptable salt thereof or the stereoisomer or tautomer thereof according to claim 1, wherein R₁ is NH₂.

3. The compound, the pharmaceutically acceptable salt thereof or the stereoisomer or tautomer thereof according to claim 1, wherein R₂ is selected from the group consisting of Cl and Br.

4. The compound, the pharmaceutically acceptable salt thereof or the stereoisomer or tautomer thereof according to claim 1, wherein R₃ is H.

5. The compound, the pharmaceutically acceptable salt thereof or the stereoisomer or tautomer thereof according to claim 1, wherein R₄ is selected from the group consisting of Cl and Br.

6. The compound, the pharmaceutically acceptable salt thereof or the stereoisomer or tautomer thereof according to claim 1, wherein R₅ is F.

7. The compound, the pharmaceutically acceptable salt thereof or the stereoisomer or tautomer thereof according to claim 6, wherein the structural unit

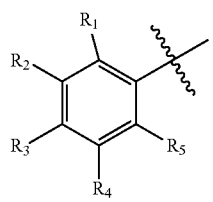

is selected from the group consisting of

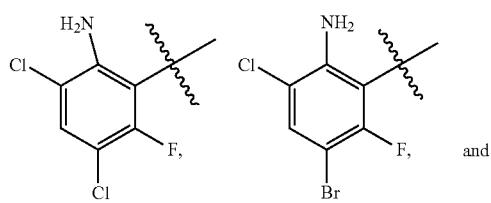

-continued

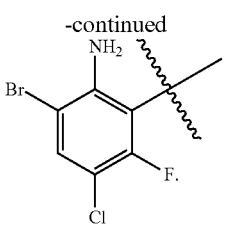

8. The compound, the pharmaceutically acceptable salt thereof or the stereoisomer or tautomer thereof according to claim 1, wherein R₆ is selected from the group consisting of H, F, Cl, Br, I, CH₃, CF₃, CHF₂ and CH₂F.

9. The compound, the pharmaceutically acceptable salt thereof or the stereoisomer or tautomer thereof according to claim 8, wherein R₆ is selected from the group consisting of CF₃ and CH₃.

10. The compound, the pharmaceutically acceptable salt thereof or the stereoisomer or tautomer thereof according to claim 1, wherein R₉ is selected from the group consisting of H, Cl,

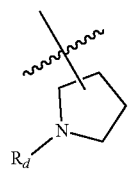

and C₁₋₄ alkylamino.

11. The compound, the pharmaceutically acceptable salt thereof or the stereoisomer or tautomer thereof according to claim 10, wherein R₉ is selected from the group consisting of H, Cl,

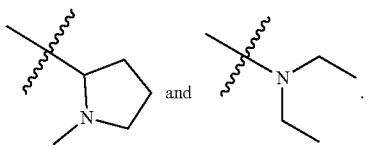

12. The compound, the pharmaceutically acceptable salt thereof or the stereoisomer or tautomer thereof according to claim 1, wherein the structural unit

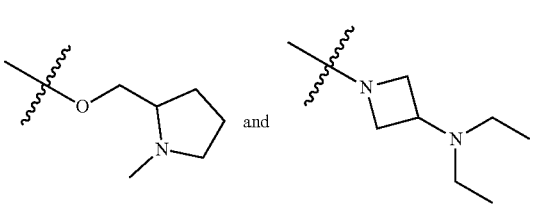

is selected from the group consisting of H, Cl,

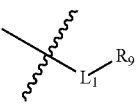

13. The compound, the pharmaceutically acceptable salt thereof or the stereoisomer or tautomer thereof according to claim 1, wherein $R_{10}$ is selected from the group consisting of H and

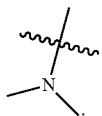

14. The compound, the pharmaceutically acceptable salt thereof or the stereoisomer or tautomer thereof according to claim 1, wherein the structural unit -$L_2$-$L_3$-$R_{10}$ is selected from the group consisting of H,

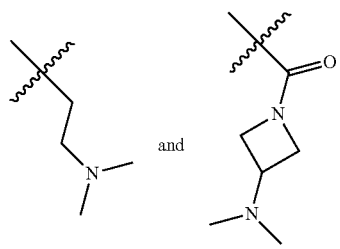

15. The compound, the pharmaceutically acceptable salt thereof or the stereoisomer or tautomer thereof according to claim 1, wherein the compound is selected from formula (I):

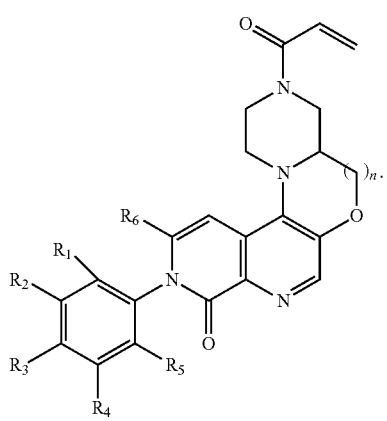

(I)

16. The compound, the pharmaceutically acceptable salt thereof or the stereoisomer or tautomer thereof according to claim 1, wherein the compound is selected from any one of:

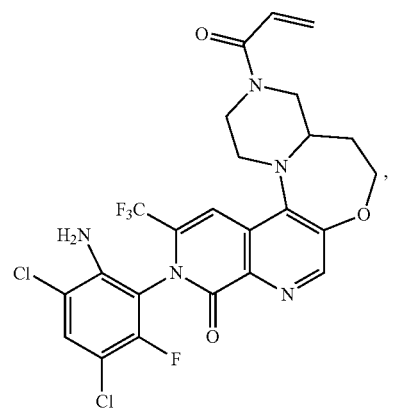

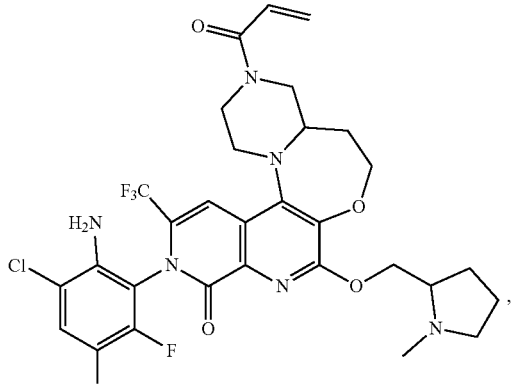

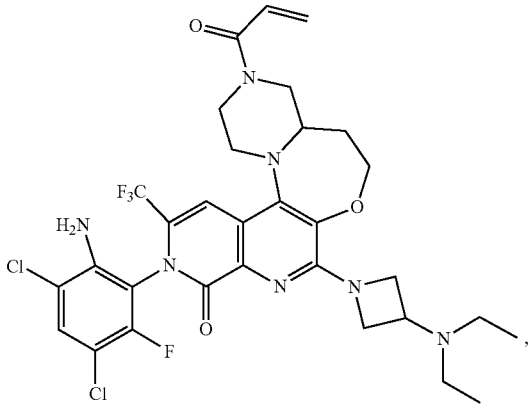

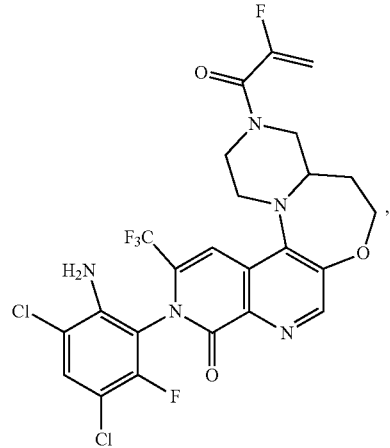

31
-continued
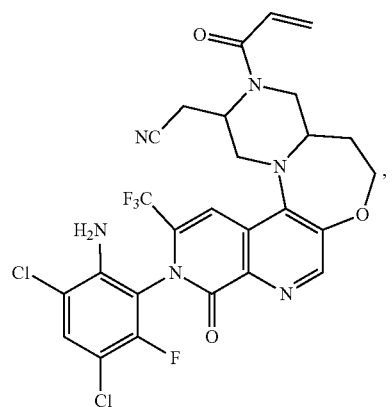
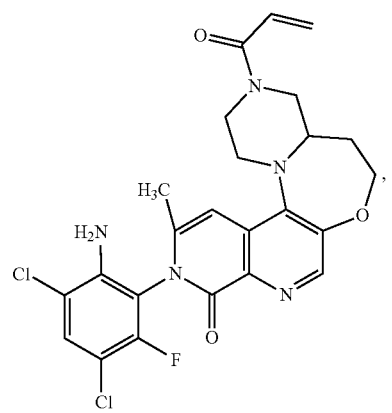
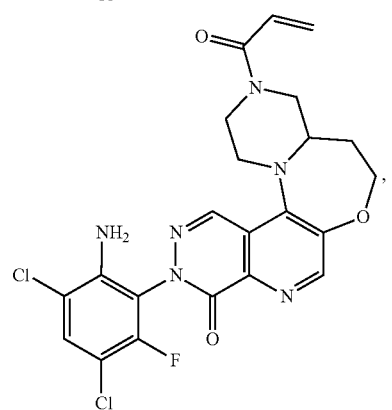
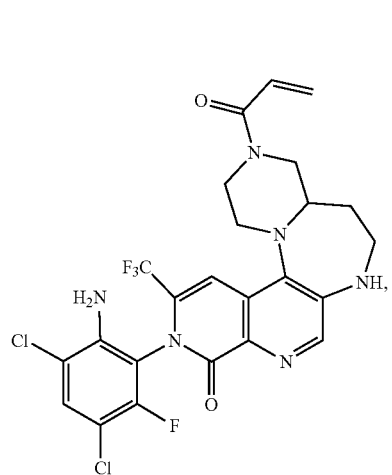
32
-continued
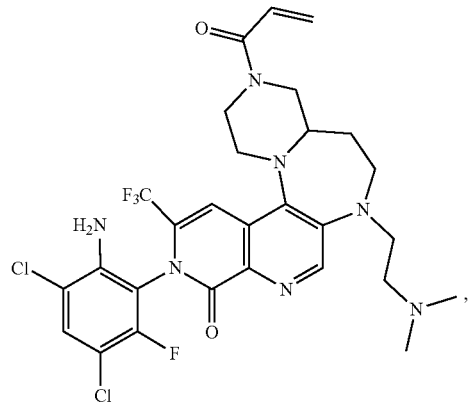
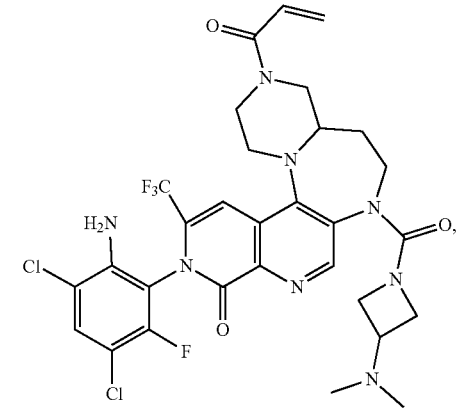
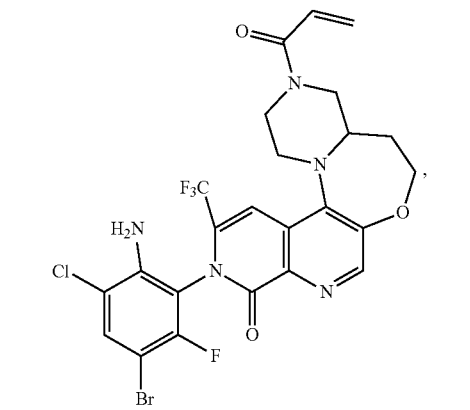
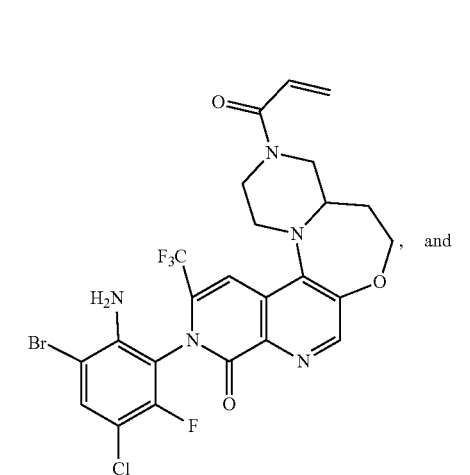
and -continued
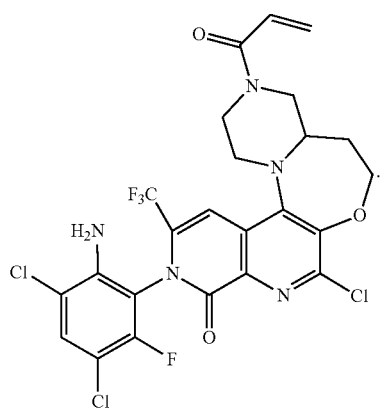 [SMILES: C=CC(=O)N1CCN2c3c(c(Cl)nc4c(=O)n(-c5c(N)c(Cl)cc(Cl)c5F)c(C(F)(F)F)cc34)OCCC2C1]
17. The compound, the pharmaceutically acceptable salt thereof or the stereoisomer or tautomer thereof according to claim 16, selected from the group consisting of:
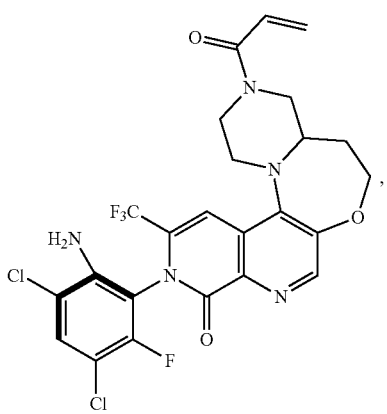
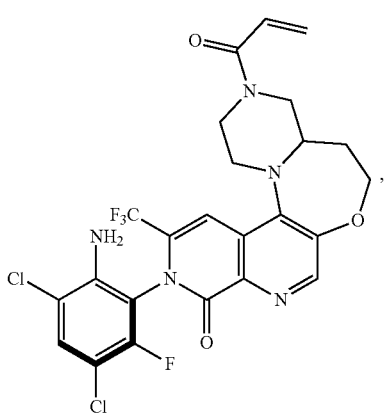
-continued
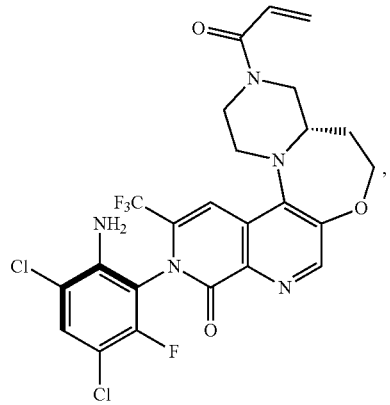
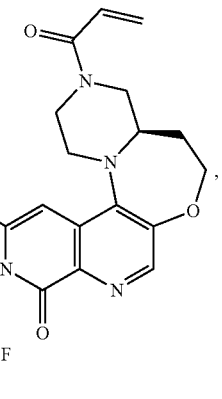
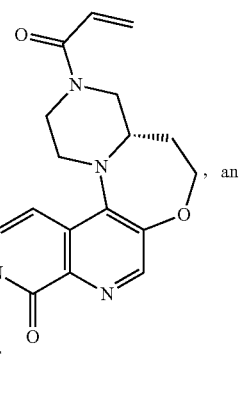, and
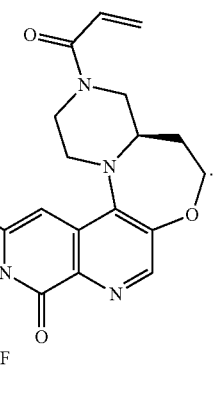
18. A pharmaceutical composition, comprising a therapeutically effective amount of the compound or the pharmaceutically acceptable salt, or the stereoisomer or tautomer thereof according to claim 1 as an active ingredient, and a pharmaceutically acceptable carrier.

19. A method for treating KRAS G12C-associated cancer, comprising administering to a subject in need thereof a compound, a pharmaceutically acceptable salt, or an stereoisomer or tautomer thereof according to claim 1.

* * * * *